US012693222B2

(12) United States Patent (10) Patent No.: US 12,693,222 B2
League et al. (45) Date of Patent: Jul. 28, 2026

(54) DETECTION SYSTEMS AND METHODS OF USE THEREOF

(71) Applicant: Enterprise Sensor Systems, LLC, Franklin, TN (US)

(72) Inventors: Alfred W. League, Travelers Rest, SC (US); Damien A. Kerr, Frederick, MD (US)

(73) Assignee: Enterprise Sensor Systems, LLC, Franklin, TN (US)

( * ) Notice: Subject to any disclaimer, the term of this patent is extended or adjusted under 35 U.S.C. 154(b) by 609 days.

(21) Appl. No.: 17/926,463

(22) PCT Filed: May 19, 2021

(86) PCT No.: PCT/US2021/033220

§ 371 (c)(1),
(2) Date: Nov. 18, 2022

(87) PCT Pub. No.: WO2021/236807

PCT Pub. Date: Nov. 25, 2021

(65) Prior Publication Data

US 2023/0184682 A1 Jun. 15, 2023

Related U.S. Application Data

(60) Provisional application No. 63/026,762, filed on May 19, 2020.

(51) Int. Cl.
*G01N 21/64* (2006.01)
*A61L 2/10* (2026.01)
*G01N 33/497* (2006.01)

(52) U.S. Cl.
CPC ............ *G01N 21/6456* (2013.01); *A61L 2/10* (2013.01); *G01N 33/497* (2013.01); *G01N 2201/06113* (2013.01)

(58) Field of Classification Search
None
See application file for complete search history.

(56) References Cited

U.S. PATENT DOCUMENTS

| | | | | |
|---|---|---|---|---|
| 2003/0123056 A1* | 7/2003 | Barnes | ................. | G01J 3/2823 356/51 |
| 2004/0161804 A1* | 8/2004 | McCash | ............ | G01N 33/5695 435/7.2 |
| 2020/0134520 A1* | 4/2020 | Kantor | ................. | G07C 11/00 |

FOREIGN PATENT DOCUMENTS

| | | | | | |
|---|---|---|---|---|---|
| CA | 2910348 C | * | 5/2017 | .......... | A61G 10/023 |
| CN | 1305485 A | * | 7/2001 | ............... | C07F 9/58 |
| RU | 2367977 C1 | * | 9/2009 | | |
| WO | WO-2013116316 A1 | * | 8/2013 | ........... | G01J 3/0267 |
| WO | WO-2018170155 A1 | * | 9/2018 | ........... | G06Q 50/26 |

* cited by examiner

*Primary Examiner* — Andrew Smyth

(57) ABSTRACT

Detection systems and methods of use thereof, and, in particular, hyperspectral fluorescence systems and methods for detecting aerosolized viral biologics and/or carcinogenic compounds or elements. The system utilizes, and the method is, a non-invasive, immediate, and non-biohazard byproduct method (with the actual imaging to determination generally occurring in less than 3 seconds) with a throughput of the station in around ten seconds (which is allowing for sanitization of the station before and after each individual is tested).

17 Claims, 4 Drawing Sheets

| Step 301: | Sterilize/disinfect station |
| Step 302: | Individual enters and positioned in station |
| Step 303: | Individual breathes into sampling area |
| Step 304: Use Hyperspectral camera/sensor to gather data |
| Step 305: | Individual leaves station |
| Step 306: | Sterilize/disinfect station |
| Step 307: | Determine presence of spectral signature |
| Step 308: | Next stage testing |

DETECTION SYSTEMS AND METHODS OF USE THEREOF

RELATED PATENTS/PATENT APPLICATIONS

This application is a 35 U.S.C § 371 national application of PCT Application No. PCT/US21/33220, filed on May 19, 2021, entitled "Detection Systems And Methods Of Use Thereof", which claims priority to U.S. Provisional Patent Appl. Ser. No. 63/026,762, filed May 19, 2020, to Alfred W. League and Damien A. Kerr, and entitled "Integration And Application Of Multilayered Technology To Screen Individuals For Presence Of Infectious Indicators In Exhalation Through Spectral Analysis" (and alternative entitled "COVID Finder"). These patent applications are commonly owned by the owner of the present invention and are hereby incorporated herein by reference in their entirety for all purposes.

TECHNICAL FIELD

The present invention relates to detection systems and methods of use thereof, and, in particular, hyperspectral fluorescence systems and methods for detecting aerosolized viral biologics and/or carcinogenic compounds or elements.

BACKGROUND

Recently, the wide spread of infectious diseases, such as COVID-19, and the expansion of a range of infections are at the forefront of serious challenges to humanity. To solve problems for public heath, there has been a demand for a highly precise and simple system method for detecting the viral loads of an individual in real time/near real time. In quarantine inspection, a cleaning liquid from an individual's nasal cavity is analyzed. However, such inspection method has problems in sensitivity and latency of diagnosis. Moreover, to take measures against pandemic and bio terrors, viruses and bio hazards in the atmosphere need to be inspected constantly. In a manual inspection method conducted by a human being, such as inspecting the cleaning liquid from the nasal cavity, it is difficult to expect the automation of the virus analysis and is limited to the specific hazard being tested for, while creating biohazard and potential infectious substances that can act additional spreading vectors As for the analysis of, e.g., COVID-19, the current methods of observing and analyzing have drawbacks in that it takes time (in some instances several days) for detection to be made, and it is typically difficult to automate such method. During the period of latency, the contagion could unknowingly be spreading at exponential rates. Additionally, results are only valid at time of sampling, so it is feasible that immediately after testing, exposure could occur, yet tests would report a negative result, contributing to accelerated unknowing and untraceable infection spread. For instance, U.S. Pat. No. 8,911,955, entitled Virus Detection Device and Virus Detection Method," issued Dec. 16, 2014 to Tamura et al., is directed to a virus detection device that includes a diffusion unit configured to diffuse a virus in a gas as an inspection target into an aqueous solution containing a fluorescent antibody specifically adsorptive to the virus by bringing the gas into contact with the aqueous solution and configured to adsorb the fluorescent antibody to the virus in the gas; an atomization unit configured to atomize the aqueous solution and generate a mist group of the aqueous solution in which the gas is diffused; a fluorescence measuring unit configured to measure a fluorescence intensity of the mist group; and an air current generator configured to form an air current flowing toward the fluorescence measuring unit from the atomization unit.

Further for instance, U.S. Patent Publ. No. 2020/0163505, entitled "Detection Device," published May 28, 2020, to Nakayama et al., is directed to a detection system whereby a virus or the like can be effectively detected in order to suppress the spread of infectious disease by the virus or the like. The detection system of this patent application includes an autonomous collection device that is capable of moving on a floor surface and for collecting an object on the floor surface, and a station device for detecting an analyte from the object collected from the floor surface by the autonomous collection device. The autonomous collection device includes a moving part for moving on the floor surface, a primary electric blower for sucking the object on the floor surface, and a dust container for storing the sucked object. The station device includes a transfer pipe fluidically connected to the dust container of the autonomous collection device when the autonomous collection device is positioned in a home position, and a virus detection part for detecting the analyte from the object transferred from the dust container through the transfer pipe.

Such devices and methods continue to have the same drawbacks, which render them difficult to automate and use. Moreover, the current efforts remain focused upon invasive testing, symptom recognition, treatment, and vaccine development.

Accordingly, the need remains for a system and method to detect viral loads and carcinogenic compounds or elements, particularly in real time/near real time and in a manner that can be repeatedly performed in a simple and safe manner. Moreover, a need remains for improving the confidence in determining quickly and accurately the presence of viral biologics and/or carcinogenic compounds or elements, such as when traveling on public transportation like airplanes, buses, and ships. Furthermore, the need remains for a system and method having the ability for dynamic updating to not only current, but new emerging threats, without hardware/chemical modification.

SUMMARY OF THE INVENTION

The present invention relates to detection systems and methods of use thereof, and in particular, hyperspectral fluorescence systems and methods for detecting aerosolized viral biologics and/or carcinogenic compounds or elements.

In general, in one aspect, the invention features a detection system that includes a station having a sampling area through which an aerosolized sample can be passed. The aerosolized sample is a breath exhalation from an individual in proximity to the station. The detection system further includes one or more hyperspectral fluorescent cameras positioned for measuring fluorescence of components in the aerosolized sample after excitation of the aerosolized sample in an excitation region. The sampling area and excitation region overlap at least in part. The detection system further includes one or more processors that collectively are operatively connected to the one or more hyperspectral fluorescent cameras for receiving information from the one or more hyperspectral fluorescent cameras related to fluorescence of the components in the aerosolized sample measured by the one or more hyperspectral fluorescent cameras.

Implementations of the invention can include one or more of the following features:

The one or more processors can be collectively operable for determining, within near real time, a spectral signature of one or more of the components in the aerosolized sample.

The one or more processors can be collectively operable for determining, within near real time, the presence of one or more particular components in the aerosolized sample based upon the determined spectral signature. The particular component can be selected from a group consisting of viral biologics, carcinogenic compounds and elements, and combinations thereof.

The detection system can further include a laser excitation emitter positioned to excite the components of the aerosolized sample in the excitation region.

The laser excitation emitter can include a laser having a wavelength in the range of 200 nm to 1200 nm.

The laser excitation emitter can include a laser having a wavelength in the range of 235 nm to 500 nm.

The laser excitation emitter can include a laser having a wavelength of 405 nm.

The laser excitation emitter can be integral with one of the one or more hyperspectral fluorescent cameras.

The detection system can further include a UV-light emitter positioned in proximity of the station capable of sterilizing or disinfecting the station before and after the breath exhalation of the individual.

The UV-light emitter can have an illumination wavelength of 222 nm.

The detection system can further include an infrared camera capable of measuring temperature of the individual in close proximity of the station.

The individual in close proximity of the station can be within the station.

The station can include a light display that is capable of indicating to the individual when to enter and when to exit the station.

The particular component can be a viral biologic.

The viral biologic can be COVID-19.

The station can be a permanent structure.

The station can be a deployable structure that is capable of being moved from one position to another.

The detection system can further include a power source that is solar powered or battery powered.

The detection system can be located at a portal of movement.

The portal of movement can be selected from a group consisting of airport, bus, or boat terminals, stadiums, concerts, restaurants, public gathering places, places of worship, theatres, office buildings, commercial stores, government facilities, hospitals, and medical facilities.

The detection system can be located at a point of sale for over-the-counter medication and/or prescription medication.

Near real time can be less than 3 seconds.

The detection system can be capable of being used for detection of different aerosolized samples in less than 10 seconds.

In general, in another aspect, the invention features a method that includes permitting an individual to come in close proximity with a station of a detection system. The method further includes permitting the individual to exhale breath to produce an aerosolized sample that flowably passes through a sampling area in the station. The method further includes utilizing one or more hyperspectral fluorescent cameras to measure the fluorescence of components in the aerosolized sample after excitation of the aerosolized sample in an excitation region. The sampling area and excitation region overlap at least in part. The method further includes transmitting the information measured by the one or more hyperspectral fluorescent cameras to one or more processors.

Implementations of the invention can include one or more of the following features:

The method can further include determining, within near real time and using the one or more processors a spectral signature of one or more of the components in the aerosolized sample.

The method can further include determining, within near time and using the one or more processors, the presence of one or more particular components in the aerosolized sample based upon the determined spectral signature. The particular component can be selected from a group consisting of viral biologics, carcinogenic compounds and elements, and combinations thereof.

The method can further include using a laser excitation emitter to excite the components of the aerosolized sample in the excitation region.

The laser excitation emitter can include a laser having a wavelength in the range of 200 nm to 1200 nm.

The laser excitation emitter can include a laser having a wavelength in the range of 235 nm to 500 nm.

The laser excitation emitter can include a laser having a wavelength of 405 nm.

The laser excitation emitter can be integral with one of the one or more hyperspectral fluorescent cameras.

The method can further include using a UV-light emitter to sterilize or disinfect the station before and after the breath exhalation of the individual.

The UV-light emitter can have an illumination wavelength of 222 nm.

The method can further include using an infrared camera to measure temperature of the individual in close proximity of the station.

The step of permitting an individual to come in close proximity with a station can include the individual is permitted within the station.

The method can further include using a light display to indicate to the individual when to enter and when to exit the station.

The particular component can be a viral biologic.

The viral biologic can be COVID-19.

The station can be a permanent structure.

The station can be a deployable structure. The method can further include moving the deployable structure from one position to another.

The detection system can further include a power source that is solar powered or battery powered.

The detection system can be located at a portal of movement.

The portal of movement can be selected from a group consisting of airport, bus, or boat terminals, stadiums, concerts, restaurants, public gathering places, places of worship, theatres, office buildings, commercial stores, government facilities, hospitals, and medical facilities.

The method can further include restricting the individual from passing through the portal of movement.

The method can be utilized in a telemedicine application.

The detection system can be located at a point of sale for over-the-counter medication and/or prescription medication.

The method can further include a step of providing medication recommendation information to the individual. The medication recommendation information can include information related to a medication recommendation based upon, at least in part, the information measured by the one or more hyperspectral fluorescent cameras.

The method can further include facilitating a communication with a physician or medical practitioner who can proscribe medication based upon, at least in part, the information measured by the one or more hyperspectral fluorescent cameras.

Near real time can be less than 3 seconds.

The detection system can be used for detection of different aerosolized samples in less than 10 seconds.

The method can further include harvesting the information measured by the one or more hyperspectral fluorescent cameras with additional information. The additional information can include other information measured by the one or more hyperspectral fluorescent cameras of the detection system. The method can further include correlating the information and additional information to determine whether there is any indication of an emergence or re-emergence event taking place. The method can further include alerting one or more third parties to inform of the emergence or re-emergence event.

The additional information can include further information measured by one or more other detection systems comprising one or more hyperspectral fluorescent cameras.

The information and additional information can include spectral signature information.

The one or more third parties can include parties selected from a group consisting of government organizations, health organizations, and combinations thereof.

The alerting of the one or more third parties to inform of the emergence or re-emergence event can result in one or more restrictions being implemented by at least one of the one or more third parties.

The one or more restrictions being implemented being implemented by at least one of the one or more third parties can include restricting the migration of people.

DETAILED DESCRIPTION

Figure 1A:
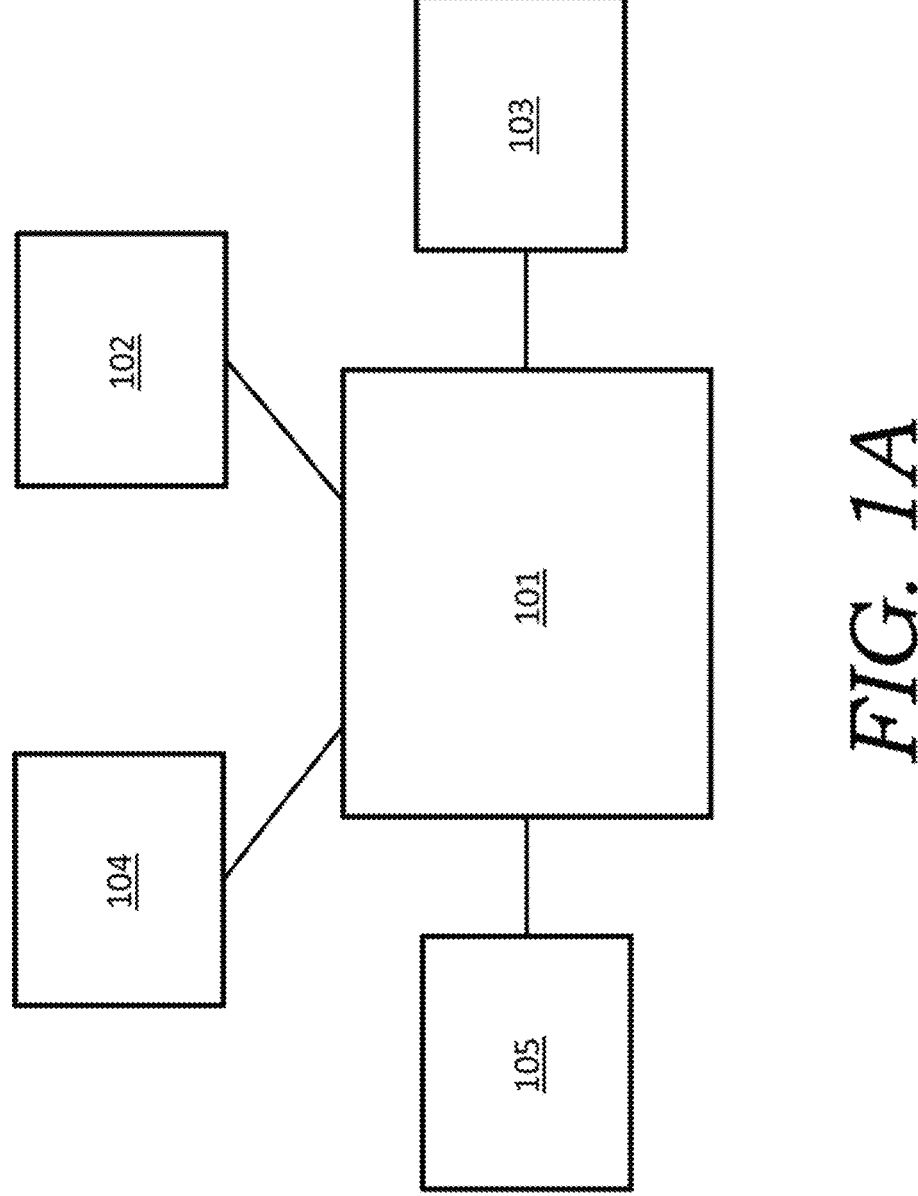
FIG. 1A is a schematic of a hyperspectral fluorescence system of the present invention.

The present invention relates to system and method for real-time detection of the presence of viral loads in an individual's breath. The present invention is focused on enabling reopening of the United States (and the World) with greater confidence and viral presence determination. Leveraging technologies from the intelligence, information, security, medical and imagery sciences, the present invention fundamentally changes how one can identify, manage, and mitigate infectious disease outbreaks in society.

The system is a hyperspectral fluorescence system that utilizes a coordinated, layered approach to identify and manage the risks of emergence/reemergence of the virus (and other communicable respiratory highly infectious diseases) at public venues, enabling non-infected individuals to continue on to transportation, into buildings, government facilities, factories, naval vessels, stadiums, theaters, etc. by sensing for presence of the virus using uniquely configured spectral cameras. A single assessment station utilizing the present invention can provide individual throughputs in less than five (5) seconds.

Embodiments of the present invention can also be used for telemedicine applications. For example, a single assessment station can be positioned at a point of sale for over-the-counter medications (such as a grocery store or a pharmacy retail store, like CVS). The system can then be used to test the customer and would be able to provide an analysis as to what specific virus the customer may be struggling with and provide a recommendation for over-the counter medication. In further embodiments, the booth would be coupled over the network provide the ability to contact a physician/medical practitioner for a consultation. This could be done via a video link (such as a Zoom consultation with the physician/medical practitioner). Based upon this consultation, the physician/medical practitioner may then be able to prescribe medication to the extent warranted under the circumstances.

Hyperspectral Imaging (HSI) is a process to capture data across the electromagnetic spectrum and identify types of material for each pixel of the imaged scene. The human eye sees color of light in what is called the visible spectrum, consisting of three light bands: red, green and blue. The HSI sensor divides the electromagnetic spectrum well beyond what is visible, into thousands of bands Since 1972, and since the launching of the USGS' LandSat multispectral imaging satellite, imagery scientists have been analyzing, studying and monitoring spectral imagery. LandSat is a highly successful multispectral satellite (MSI) with fewer bands and the width of each band is much broader. The LandSat use cases have been wide and varied for nearly 50 years, from monitoring crop health as a secondary effect to a disease, to measuring environmental degradation, to humanitarian and disaster relief. Notably, LandSat's MSI camera use case for monitoring crop health as a proxy for disease is an interesting example of the application of spectral imaging. Image scientists from the health community have employed this proxy data to determine the human health effects from plant impacted viruses.

However, there has been little spectral study on the virus/human connection directly. This has been for a variety of reasons, most notably, LandSat, SPOT, etc. and other space-based platforms, lack appropriate spectral band and ground sample distance resolution to directly study viruses in humans. The camera is too far away, and the number of spectral bands are too few. But the idea of human/virus based spectral analysis is not without merit. A ground based, close-proximity hyperspectral camera may be able to tell if someone is shedding a virus, depending on the individuals viral load, even before the individual knows that they are sick and even if they remain asymptomatic during an infection. Many viruses have an incubation period where an individual can be spreading or shedding the virus for 10 days to two weeks before showing symptoms. The influenza and corona viruses have these characteristics and currently there are no viable detection methods. The question, not clearly answered before regards the spectral signature to a symptomatic and/or an asymptomatic viral patient. (For instance, in Amin 2017, an observable difference was observed between the Raman spectra of DENV-infects sera as compared with those of healthy individuals).

There is a spectral signature to the severe acute respiratory syndrome coronavirus 2 (SARS-CoV-2), commonly known as the coronavirus or COVID-19, at the asymptomatic stage in humans. Sensors, originally developed for government and military use, specifically configured and integrated in a semi-controlled near field sensing environment, can yield non-invasive and immediate analysis and identification of the virus in the exhalation of "shedding" humans. Applying this technology enables simple near real time identification of an individual as a host to an actively growing virus and makes a cost/volume effective method for screening before entering facilities practical. By passing through portable thresholds, (like metal detectors, airport scanners, etc.) equipped with small hyperspectral imaging systems, the effluent breath, is imaged and the result is immediately compared to the viral/COVID-19 spectral signature. A match would suggest further screening is required. If no match is present, COVID-19 Virus, or other contagion, when compared to the integrated image library by the system processor, the individual is cleared to move forward.

Figure 1B:
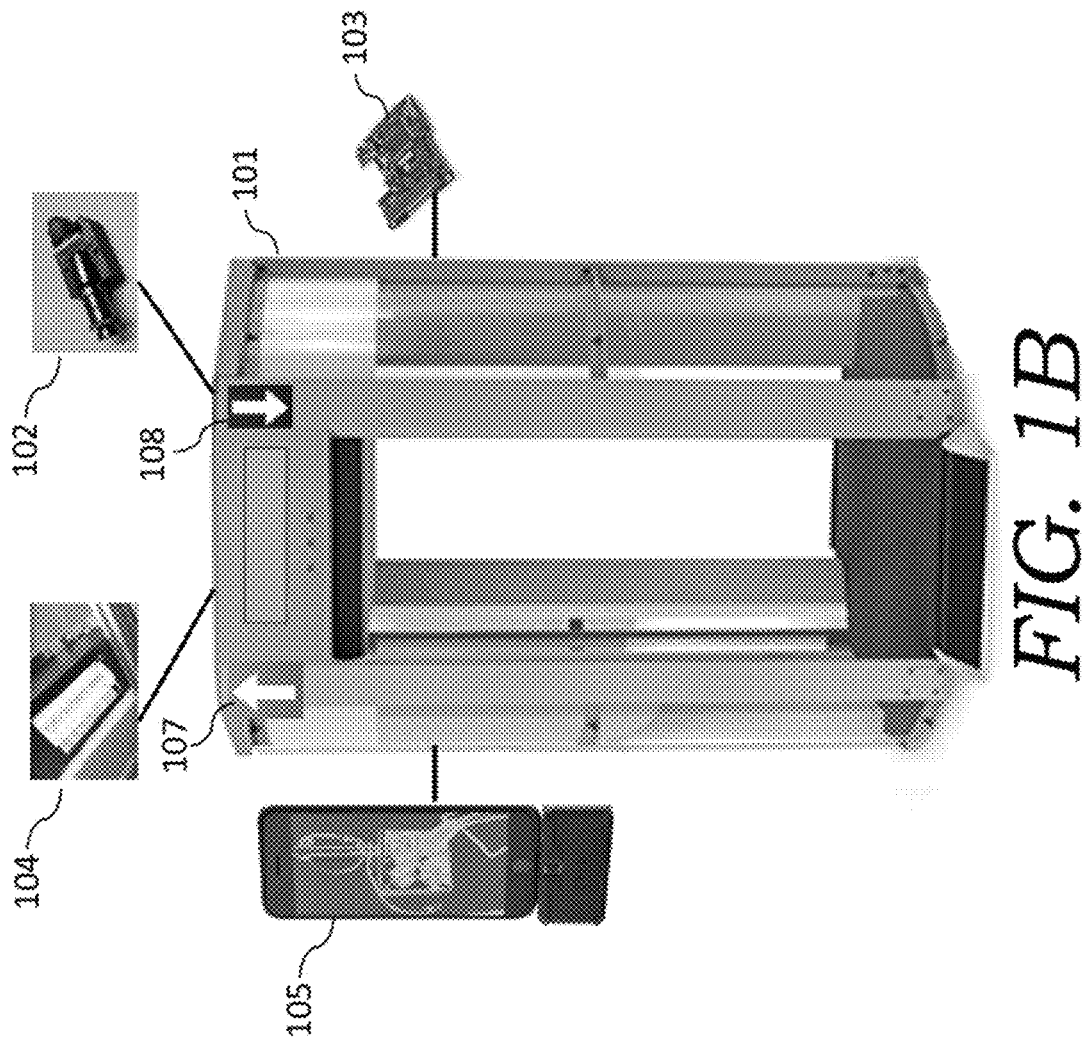
FIG. 1B is an illustration showing parts of the hyperspectral fluorescence system of FIG. 1A.

Referring to FIGS. 1A-1B, the hyperspectral fluorescence system includes a station or portal 101 that can be similar to the station or portal that is presently being used at TSA checkpoints in airport terminals. Station 101 is configured to include one or more hyperspectral camera/sensors 102 and a controller/network interface 103. Station 101 can also include a far UV-light emitter 104 and an infrared (IR) camera/sensor 105. Far UV-light emitter 104 (which can be a UV bulb for example at 222 nm) can be used for sterilizing/disinfection between uses of the station 101 to ensure a sterile environment and mitigate any cross contamination or bio-hazard. IR camera/sensor 105 (such as a forward looking infrared (FLIR) camera) can be used for precise temperatures, such as for taking the temperature of the individual being tested in the station 101. Controller/network interface 103 is a processing interface that can be utilized to control the hyperspectral camera/sensors 102, far UV-light emitter 104, and IR sensor 105.

A light panel (with green arrow 107 and red arrows 108) can be included in station 101 to provide visual indicators to the individuals being tested to enter and exit station 101 and the results of the initial analysis.

Figure 2:
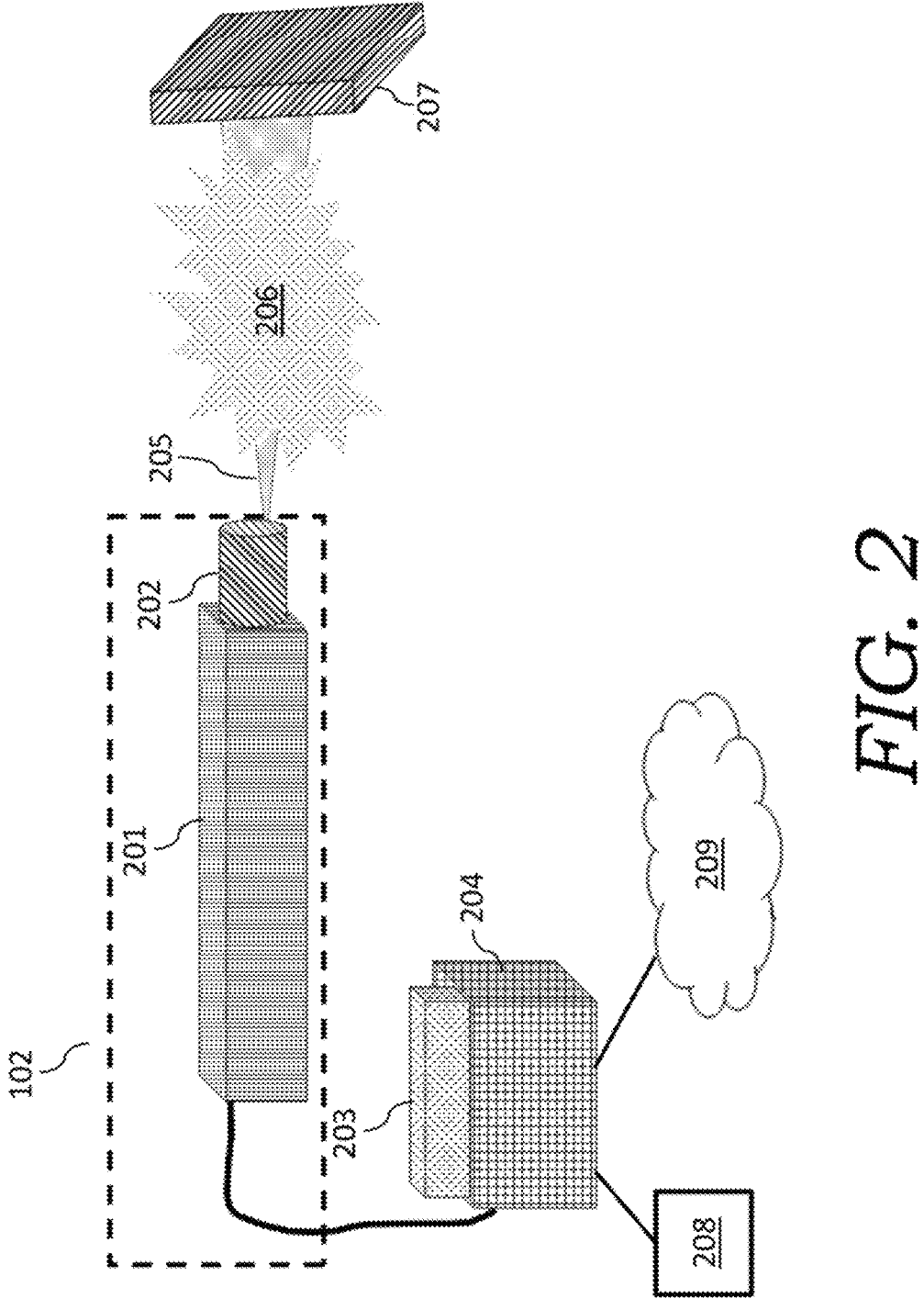
FIG. 2 is an illustration showing operation of the imaging portion a hyperspectral fluorescence system shown in FIG. 1A.

FIG. 2 shows the operation of the one or more hyperspectral cameras/sensors 102 of system 100. Hyperspectral camera/sensor 102 includes a hyperspectral fluorescent camera 201 (which can include an integrated laser excitation emitter). In some embodiments, the integrated laser excitation emitter is a 405 nm laser. In other embodiments, hyperspectral fluorescent camera 201 can utilize the excitation caused by a natural light source instead of an integrated laser). The integrated laser of hyperspectral fluorescent camera 201 emits a laser in excitation region 205. Hyperspectral camera/sensors 102 further includes a hyperspectral lens 202, which measures the wavelengths and intensity of elements, their "signature," aerosolized in the sampling area 206. A laser line light absorber 207 can be used to remove environmental refraction, and can be used to shield the individual from exposure to any of the laser light emitting from the integrated laser.

Hyperspectral camera/sensor 102 can be connected to a computer 203 (such as an industrial fan-less computer) and a camera supply module 204. In some embodiments, the computer 203 can be integrated with controller/network interface 103. The computer 203 (such as an industrial fan-less computer) and a camera supply module 204 can be connected to a network 209 (such as wirelessly or via an Ethernet connection) and can be connected to a power source 208 (such as 100 V (AC) and 5 amps). The system may be configured for permanent installation or a remote deployment configured for field operations with integration of solar/power conditioning and lithium ferrite batteries.

For instance, the hardware for this arrangement can be based upon hyperspectral fluorescence imaging system optics (such as from Middleton Spectral Vision, Middleton, Wisconsin), including a 405 nm laser projected out through the system's optics and which receives fluorescence through the same fore optics. The fluorescence is directed through a 405 nm rejection long-pass filter (approximately 415-430 nm edges). The emitted fluorescence can be directed by an infinity corrected optics onto the 80 μm input slit of a high performance hyperspectral spectrograph and onto a very sensitive scientific CMOS (sCMOS) based camera. This camera has high dynamic range for low light levels as well as capturing up to 64,000 counts of optical signal.

The camera with the basic optics can be sensitive in an approximate 2" line that can record droplets containing fluorescing materials. In some embodiments, the distance for this is about 100 mm to 250 mm (and more specifically is about 150 mm to 190 mm) from the lens of the camera system.

The supply electronics can be contained in an electrical enclosure and connected with a bundle of cables to the camera and optical system. The distance between the optical system and the supply electronics is approximately 6 ft. An industrial fan-less computer can be part of the electronic system capable of controlling the system.

As for the software for this arrangement, software (such as from Middleton Spectral Vision) can be used to control the imaging/collection head, collecting data from the system field of view. A graphical user interface can be used to select integration time, camera frame rate, and other parameters necessary for the control of the system. The hyperspectral data cube can be saved on the large capacity hard drive of the system for further processing and analysis by hyperspectral visualization software on the system computer, capable of visualizing and analyzing the resulting data. The output of the measurement can be the fluorescence as a function of time in a hypercube of data in an industry standard ENVI file format.

The arrangement shown in FIGS. 1A-1B and 2 can be used for measuring biological components, identifying presence or absence of components in samples within the area of its focal line. As an individual being tested in station 101 can breathe (i.e., aerosolized breadth) into sampling area 206, which is excited by integrated laser excitation emitter in excitation region 205, and the hyperspectral camera/sensor 102 can then gather date used for measuring.

Working with the medical, science, imagery/spectral sciences and information community, hyperspectral fluorescence system uses three layers of technology application to discover infectious disease though exhalation.

The first layer is includes station 101, which is used as a "point of passage" that is like a walk-through metal detector or body scanner commonly at TSA checkpoints and public building access points) allowing discovery of asymptomatic carriers from their exhalation and referring them for immediate testing. Since this is similar to the operation implementations utilized at TSA checkpoints today, this first layer should be easily understood by the individuals being tested and can be readily taught to TSA personnel and the like for running the tests using station 101.

The spectral image gathered using station 101 can be compared to library references for the presence (or non-presence) of infectious presence in the aerosolized exhalation of the individual via a laptop computer using spectral processing algorithms. New viral signatures can be added as necessary for future outbreaks or mutations as software library updates. For example, the information can be gathered to detect the presence of the spectral signature of COVID-19 in the aerosolized exhalation of the individual being tested. These can be determined in real time or near real time (less than a minute, generally less than 5 second, and more generally less than 3 seconds).

The second layer includes a next stage "point of care" testing using spectrometry to match "shedding viruses" (and other respiratory diseases on the spot), with results in real time/near real time.

The third layer includes data harvesting, having correlating and alerting anticipatory information capability that constantly monitors global data sources for indicators of emergence and re-emergence before they establish, allowing more mitigation.

Figure 3:
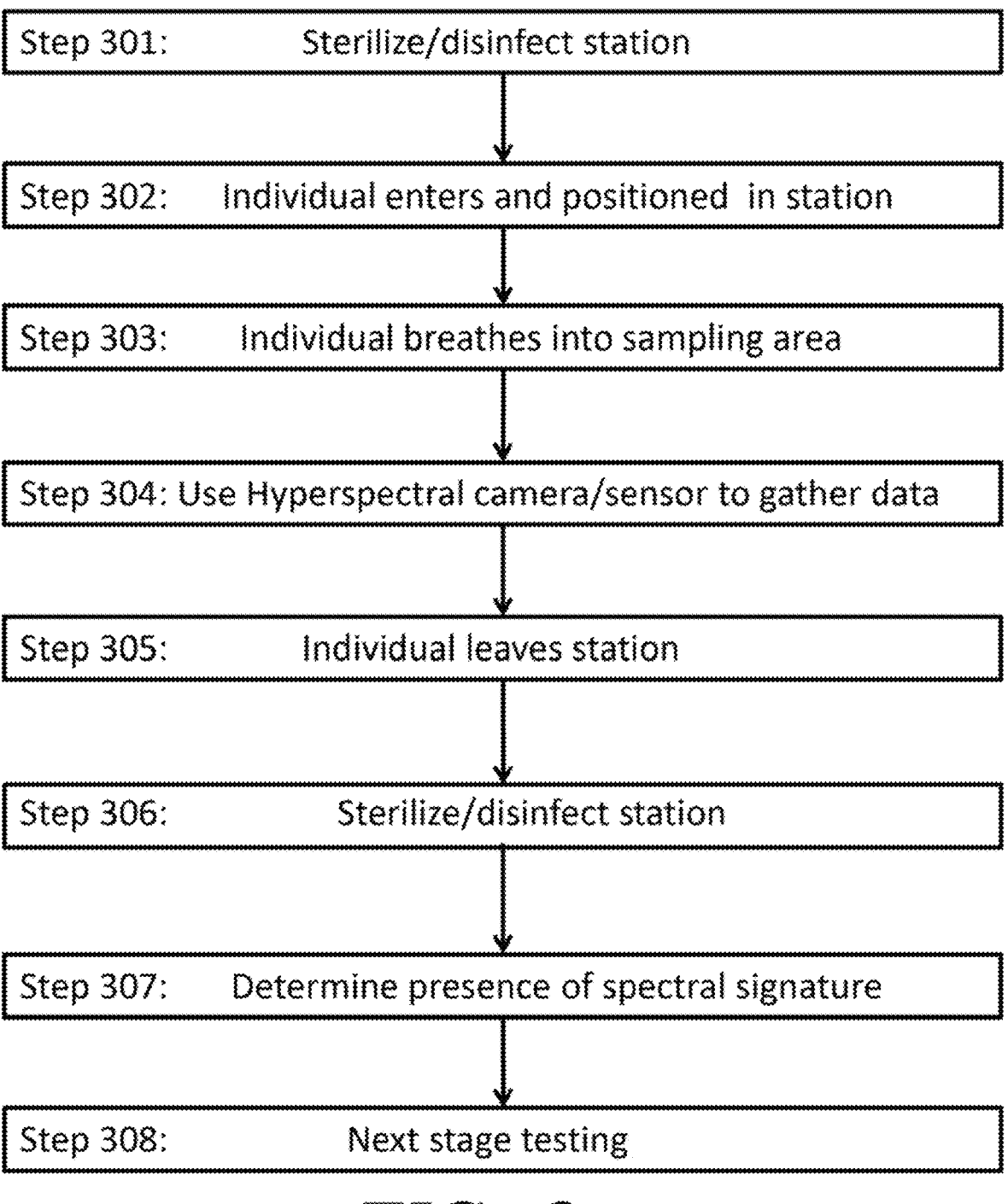
FIG. 3 is a flowchart of a method utilizing a hyperspectral fluorescence system of the present invention.

FIG. 3 shows a flowchart of a method utilize a hyperspectral fluorescence system of the present invention.

In step 301, the station is first sterilized and disinfected, such as using UV-light emitter.

In step 302, an individual then enters the station and positions themselves properly within the station. This can be done by having an outline of where the individual is supposed to stand, similar to as in a typical airport detectors currently in use at airports. Optionally, while the individual is in the station, the temperature of the individual can be measures, such as by using the FLIR camera.

In step, 303, the individual breathes into the sampling area. This can then be excited, such as by emission from the integrated laser of hyperspectral fluorescent camera, in the excitation region.

In step 304, the hyperspectral camera/sensors are used to gather data.

In step 305, the individual leaves the station.

In step 306, the station is again sterilized and disinfected, such as using UV-light emitter, so that the station is ready of the next individual to be tested.

In step 308, the information gathered is analyzed to determine the presence (or lack of presence of the targeted spectral signatures or signatures. Again this can occur in real time/near real time.

In step 309, if warranted, next stage testing can be performed.

Such determining of respiratory viral load is via non-invasive, immediate, and non-bio hazard byproduct method (with the actual imaging to determination generally occurring in less than 3 seconds) with a throughput of the station in around ten seconds (which is allowing for sanitization of the station before and after each individual is tested.)

This approached can be utilized for a scalable operation solution in a broad array of applications. For example, layers one and 2 are operationally deployed to support a multiple of objectives, with capabilities including:

screening workers arriving for work;
  screening of fans attending sporting events, concerts, etc.
  screening of shoppers entering stores, restaurants, malls, etc.
  screening of students entering schools;
  screening of patients and visitors entering hospitals and medical facilities; and
  screening of personnel before deployment in defense of National Security.

While direct screening is critical, understanding where "waves" or new outbreaks may occur based on a broader "indications and warnings" capacity is crucial as well. The third layer, while informed by the first and second layers, can use a much larger swath of data to understand the perhaps suggests that an area/region needs to cue up resources or lock down.

The present invention provides for the isolation, unique spectral identification, and deployment of a novel diagnostic technique that can be deployed to portals of movement (airports, stadiums, public gathering places, etc.). Moreover, once deployed, a broader spectral library can be developed as a method of screening for other infectious diseases simultaneously.

Furthermore, because this form factor and individual screening methods are similar to those already being used in portals of movement, most individuals are already used to these types of non-invasive procedures, offering reduced adoption friction, cost effective screening, with equipment that is readily available and easily procurable.

The present invention thus provides a capability to rapidly screen individuals at the early onset of new infectious viruses (as a tripwire to discover and alert) and diseases via minute effluent breath detection and analysis. It can also be employed to ensure continued monitoring reducing the likelihood of re-occurrence. This capability offers the benefit to reduce and control the spread and transmission of virus, disease, and lead to non-invasive diagnostic protocols for respiratory ailments.

For instance, by way of example, if another new infectious virus were to emerge like COVID-19 did in the end of 2019 and early 2020, the spectral signature of the new infectious virus could be quickly determined, and this spectral signature could then be used in embodiments of the present invention to identify and quarantine individuals (and prevent them from migrating to reduce the spread of the virus). Moreover, as this would then utilize existing equipment, it could be disseminated rapidly.

REFERENCES

Amin, A., et al., "Identification of new spectral signatures associated with dengue virus infected sera: Identification of new spectral signature," *Journal of Raman Spectroscopy*, 2017, 48(5) (DOI: 10.1002/jrs 5110) ("Amin 2017").

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, other embodiments are within the scope of the following claims. The scope of protection is not limited by the description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

Amounts and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about" and "substantially" when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "substantially perpendicular" and "substantially parallel" is meant to encompass variations of in some embodiments within ±10° of the perpendicular and parallel directions, respectively, in some embodiments within ±5° of the perpendicular and parallel directions, respectively, in some embodiments within ±1° of the perpendicular and parallel directions, respectively, and in some embodiments within ±0.5° of the perpendicular and parallel directions, respectively.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

What is claimed is:

1. A walk-through detection system comprising:
a station comprising:
a sampling area through which an aerosolized sample is passed, wherein the aerosolized sample is a breath exhalation from an individual in proximity to the station,
a first opening and a second opening, through which a human walks to enter and exit the sampling area, respectively,
a hyperspectral fluorescent camera configured to measure a fluorescence of components of the aerosolized sample, and
a UV-light emitter in proximity to the station, wherein the UV-light emitter is configured to sterilize the station; and a processor in communication with the hyperspectral fluorescent camera, wherein the processor is configured to receive information related to the fluorescence from the hyperspectral fluorescent camera,
wherein the walk-through detection system is capable of receiving the aerosolized sample, processing the sample, and sterilizing the sampling areas in less than 10 seconds.

2. The walk-through detection system of claim 1, wherein the processor is configured to:
determine, within a near real-time, a spectral signature of a component of the components.

3. The walk-through detection system of claim 2, wherein the processor is configured to:
identify, within near real-time, a presence of the component in the aerosolized sample based on the spectral signature, wherein the component is selected from a group consisting of viral biologics, carcinogenic compounds, and elements thereof, and combinations thereof.

4. The walk-through detection system of claim 1, wherein the walk-through detection system further comprises:
a laser excitation emitter configured to excite the components of the aerosolized sample in an excitation region.

5. The walk-through detection system of claim 4, wherein the laser excitation emitter comprises:
a laser having a wavelength in a range of 200 nm to 1200 nm.

6. The walk-through detection system of claim 4, wherein the laser excitation emitter comprises:
a laser having a wavelength in a range of 235 nm to 500 nm.

7. The walk-through detection system of claim 4, wherein the laser excitation emitter comprises:
a laser having a wavelength of 405 nm.

8. The walk-through detection system of claim 4, wherein the laser excitation emitter is integral with the hyperspectral fluorescent camera.

9. The walk-through detection system of claim 1, wherein the UV-light emitter has an illumination wavelength of 222 nm.

10. The walk-through detection system of claim 1, wherein the individual is in the station.

11. The walk-through detection system of claim 10, wherein the station comprises:
a light configured to indicate to the individual when to enter and when to exit the station.

12. The walk-through detection system of claim 2, wherein the component is a viral biologic.

13. The walk-through detection system of claim 12, wherein the viral biologic is COVID-19.

14. The walk-through detection system of any of claim 2, wherein the near real-time is less than 3 seconds.

15. The walk-through detection system of claim 1, wherein the processor is configured to:
harvest the information with additional information measured by the hyperspectral fluorescent camera;
identifying one or more of an emergence or re-emergence of a threat by correlating the information and additional information; wherein the threat comprises one or more of a biological hazard, a virus, a carcinogen, or a disease; and
alert a third party of the one or more of the emergence or re-emergence of the threat.

16. The walk-through detection system of claim 1, wherein:

the hyperspectral fluorescent camera is configured to measure the fluorescence of components after an excitation of the aerosolized sample in an excitation region, and the sampling area and the excitation region overlap.

17. The walk-through detection system of claim 4, wherein the laser excitation emitter is integral with the hyperspectral fluorescent camera.

\* \* \* \* \*